United States Patent [19]

Iriuchijima et al.

[11] Patent Number: 4,849,438
[45] Date of Patent: Jul. 18, 1989

[54] 1,2-BENZOISOTHIAZOL-3(2H)-ONE 1,1-DIOXIDE, ION(1-),2-HYDROXY-N,N,N-TRIMETHYL-ETHANAMINIUM WHICH IS PLANT PROTECTION AGENT FOR CONTROL OF FUNGI AND BACTERIA

[75] Inventors: Shinobu Iriuchijima, Yamato; Nobuo Onodera, Hiratsuka; Shunnosuke Watanabe, Higashikurume; Hiroshi Tabata, Tokyo, all of Japan

[73] Assignees: Agro-Kanesho Co., Ltd.; Denki Kagaku Kogyo Kabushiki Kaisha, both of Tokyo, Japan

[21] Appl. No.: 198,296

[22] Filed: May 25, 1988

[30] Foreign Application Priority Data

Nov. 18, 1987 [JP] Japan .................. 62-290833

[51] Int. Cl.$^4$ .................. A01N 43/80; C07D 275/06
[52] U.S. Cl. .................. 514/373; 548/210; 548/211
[58] Field of Search .................. 548/210, 211; 514/373

[56] References Cited

U.S. PATENT DOCUMENTS

| | | | |
|---|---|---|---|
| 2,725,326 | 11/1955 | Shibe, Jr. et al. | 514/373 |
| 2,803,651 | 8/1957 | Whiston et al. | 564/293 |
| 3,392,115 | 7/1968 | Shibe, Jr. et al. | 514/373 X |
| 3,970,755 | 7/1976 | Gazzard et al. | 514/373 |

FOREIGN PATENT DOCUMENTS

| | | | |
|---|---|---|---|
| 39-1243 | 2/1964 | Japan | 548/211 |
| 0117627 | 11/1974 | Japan | 514/373 |
| 00736443 | 9/1955 | United Kingdom | 544/272 |

*Primary Examiner*—Anton H. Sutto
*Assistant Examiner*—Diana G. Rivers
*Attorney, Agent, or Firm*—Oblon, Spivak, McClelland, Maier & Neustadt

[57] ABSTRACT

1,2-benzoisothiazol-3(2H)-one, 1,1-dioxide, ion(1-),2-hydroxy-N,N,N-trimethyl-ethanaminium represented by the following formula (I):

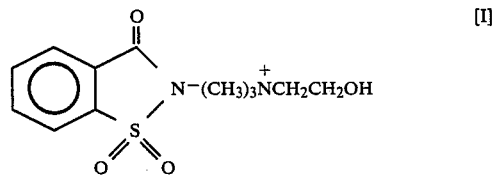

is found to have great utility as an effective component in plant protection agents for control of fungi and bacteria. By the use of the compound, diseases or blights of plants can be effectively prevented.

6 Claims, No Drawings

1,2-BENZOISOTHIAZOL-3(2H)-ONE 1,1-DIOXIDE, ION(1-),2-HYDROXY-N,N,N-TRIMETHYL-ETHANAMINIUM WHICH IS PLANT PROTECTION AGENT FOR CONTROL OF FUNGI AND BACTERIA

BACKGROUND OF THE INVENTION:

1. Field of the Invention

The present invention relates to a novel compound, 1,2-benzoisothiazol-3(2H)-one 1,1-dioxide, ion(1-),2-hydroxy-N,N,N-trimethyl-ethanaminium, a process for preparing the same, and plant protection agents containing the same as an effective component. The present invention also includes a method of protecting plants from various diseases of blights by the use of a plant protection agent containing the aforementioned compound.

2. Prior Art Statement;

It is known in the art that 1,2-benzoisothiazol-3(2H)-one 1,1-dioxide (hereinafter referred to as "saccharin") and salts thereof, for example, alkaline earth metal salts and ammonium salts thereof are effective as plant protection agents for control of fungi and bacteria. (In this connection, reference should be made to Japanese Patent Publication Nos. 21496/1967 and 9428/1972, Unexamined Japanese Patent Publication Nos. 5936/1973, 22624/1973, 109535/1974, 105216/1977, 110830/1977 and 72602/1987, and U.S. Pat. No. 3,280,137, if necessary.) Also known in the art that tertiary ammonium salts and quaternary ammonium salts of saccharin are of utility as plant protection agents for control of fungi and bacteria. In this connection reference should be made to Unexamined Japanese Patent Publication No. 204707/1985 and Japanese Patent Publication No. 34765/1980, if necessary.)

However, these known penetrative agents have not been applied for practical protection of plants from blights or the following reasons. Some of them are extremely poisonous to fishes or have an undesirable effect on the growth of plants, and others of them have the disadvantages that the effectiveness thereof is significantly reduced when applied to a paddy field from which water leaks out or the effectiveness thereof varies significantly depending on the condition of the soil.

Another plant protection agent for control of fungi and bacteria has been known and widely used for the agricultural applications. This known plant protection agent contains 3-allyloxy-1,2-benzoisothiazole 1,1-dioxide (available from Meiji Seika Kaisha Ltd. under the trade name of "ORYZEMATE", and is disclosed in Japanese Patent Publication No. 38080/1970 and U.S. Pat. No. 3,629,428) as an effective component. However, this known plant protection agent is expensive as compared with saccharins and the activity or effectiveness thereof for control of fungi and bacteria is not always satisfactory.

OBJECT AND SUMMARY OF THE INVENTION

An object of this invention is to provide a novel and useful compound which can be used stably for a long time to protect plants from blights without damaging the plants.

Another object of this invention is to provide an improved plant protection agent for control of fungi and bacteria which contains such a compound.

2-hydroxy-N,N,N-trimethyl-ethanaminium (hereinafter referred to as "choline") is one of the vitamin B group compounds and has been widely used as an additive to livestock feeds. In recent years, it has been found that analogous compounds of choline have a function of promoting the growth of plants.

We have prepared a novel compound by combining choline with saccharin, and found that this novel compound is effective as a fungicide and/or germicide agent to various fungi and bacteria which cause diseases or blights of plants. Particularly, when this compound is applied to soil or water on the surface of a paddy field in which rice plants are grown, for example, in an amount of 2 to 2000 g, preferably 10 to 300 g, per 10 ares, the rice blast and bacterial leaf blight appearing on the leaf parts of the rice plants grown in the paddy field can be effectively prevented. The compound of this invention does not blow away from the soil and thus can retain its effectiveness stably for a long time, while exerting advantageous effects, such as rooting promotion and tillering promotion, to exhibit remarkable effect for the prevention of blights appearing on the leaf parts extending above the ground. The present invention has been accomplished on the basis of the aforementioned finding.

Accordingly, this invention provides a novel compound, 1,2-benzoisothiazol-3(2H)-one 1,1-dioxide, ion(1-),2-hydroxy- N,N,N-trimethyl-ethanaminium represented by the following formula (I):

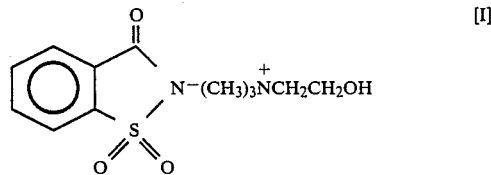

Also provided by this invention is a process for preparing 1,2-benzoisothiazol-3(2H)-one 1,1-dioxide, ion(1-),2-hydroxy-N,N,N-trimethyl-ethanaminium represented by the following formula (I):

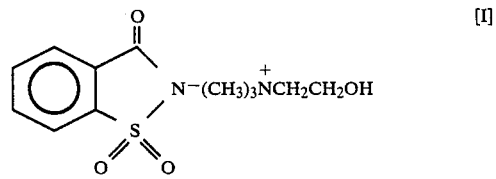

said process comprising the step of reacting 1,2-benzoisothiazol-3-(2H)-one 1,1-dioxide represented by the following formula (II):

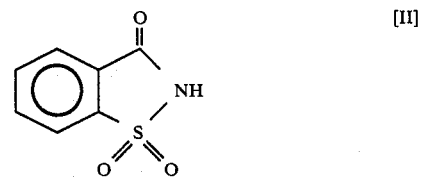

with a derivative of 2-hydroxy-N,N,N-trimethyl-ethanaminium represented by the following formula (III):

wherein X⁻ is OH⁻ or an acid group.

Further included in the scope of this invention is a plant protection agent for control of fungi and bacteria characterized by containing, as an effective component, 1,2-benzoisothiazol-3(2H)-one 1,1-dioxide, ion(1-),2-hydroxy-N,N,N-trimethyl-ethanaminium represented by the following formula (I):

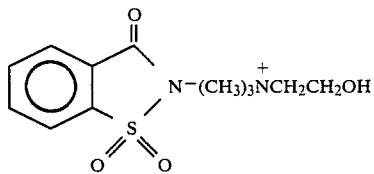

Further provided by this invention is a method of protecting plants from diseases, characterized by applying an effective amount of 1,2-benzoisothiazol-3(2H)-one 1,1-dioxide, ion(1-),2-hydroxy-N,N,N-trimethyl-ethanaminium.

DESCRIPTION OF THE INVENTION

The present invention will now be described in detail.

The compound of this invention may be synthesized by the reaction represented by the following equation:

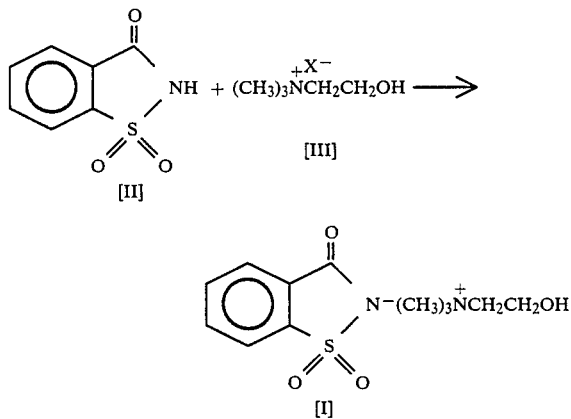

wherein X⁻ is OH⁻ or an acid group.

Each of the derivatives of choline which are represented by the general formula (III) and may be used as the starting materials for the compound of this invention has the group X⁻ which is OH⁻ or an acid group. Examples of the acid are inorganic acids, such as hydrogen chloride, hydrogen bromide, sulfuric acid, phosphoric acid and nitric acid, carboxylic acids, such as acetic acid, propionic acid, lactic acid and citric acid, and sulfonic acids, such as methanesulfonic acid and benzenesulfonic acid.

When X⁻ is OH⁻, the compound of this invention may be synthesized at high purity by reacting saccharin represented by formula (II) with a starting material (III). When X⁻ is an acid group, a base is required for neutralization. Examples of bases which may be used for this purpose include hydroxides of alkali metals, such as sodium hydroxide and potassium hydroxide, hydroxides of alkaline earth metals, such as calcium hydroxide and magnesium hydroxide, and carbonates of alkali metals, such as sodium carbonate and sodium hydrogen carbonate. From the economical point of view and reactivity, sodium hydroxide is preferred. Alternatively, sodium salt of saccharin may be used in lieu of the combination of saccharin and a base. When X⁻ is an acid group and a base is used for neutralization, a corresponding salt is formed as a byproduct. Accordingly, when it is desired to prepare the compound of this invention in a highly pure state, it is advisable to use a starting material wherein X⁻ is OH⁻.

The use of a solvent is desirous for the reaction. Usable solvents include protonic solvents, such as water, methanol, ethanol and propanol, ketone solvents, such as acetone and methyl ethyl ketone, and non-protonic solvents, such as acetonitrile, N,N-dimethylformamide, dimethylsulfoxide and N-methylpyrrolidone. It is preferred that a protonic solvent be used. Generally, the reaction proceeds approximately at room temperature. However, the reaction mixture may be heated to accelerate the reaction or to dissolve the starting materials in the solvent used. When X⁻ of the starting material (III) is OH⁻, the reaction is completed at room temperature within a short time. The solvent is then distilled off by concentration, and the concentrated product is dried in vacuum, whereby the compound of this invention is obtained as a hygroscopic crystal at a substantially stoichiometric yield.

The compound of this invention may be used directly as a plant protection agent for control of fungi and bacteria. However, it is a common practice either to dissolve or suspend it in an appropriate liquid carrier, for example, an organic solvent or to mix it with or have it adsorbed by a solid carrier, for example, a diluent or filler as is appropriate for the intended use. A variety of auxiliary agents, such as emulsifiers, stabilizers, dispersing agents, suspending agents, wetting agents and penetrating agents may be added, as desired, to form emulsions, wettable powders, granules or powders. The compound of this invention is applied generally in an amount of 2 g to 2000 g per 10 ares, preferably in an amount of 10 g to 300 g per 10 ares. For the purpose of reducing the labor for application thereof or for preventing further blights caused by various fungi and bacteria, other germicides or insecticides may be mixed therewith. When the compound of this invention is applied in an amount of effective component of 2 to 2000 g in the nursery pots or nursery beds for rice plants before they are transplanted to the paddy field, the appearance of rice blast and bacterial leaf blight can be prevented for a long time after they are transplanted to the paddy field. These blights of rice plants can be prevented for a long time after the compound of this invention is directly applied to the soil or in the water on the paddy field on which the rice plants are transplanted.

The present invention will now be described more specifically with reference to some examples thereof. However, it is to be noted here that the invention is not limited only to the following examples.

EXAMPLE 1

Synthesis of the Compound of this Invention 1.48 g (8.1 millimoles) of saccharin was added to 10 ml of methanol, and to the mixture added 2 g of an approximately 49% aqueous solution of choline hydroxide (containing 0.98 g (8.1 millimoles) of choline hydroxide) under agitation. After agitation at room temperature for about 10 minutes, all of the added saccharin was dissolved and the reaction was completed. The solvent was removed by concentration under a reduced pressure, followed by drying in vacuum, to obtain 2.36 g (containing some moisture) of the compound of this invention in the form of light brown hygroscopic crystals. The crystals were dissolved in acetone, to the solution added activated carbon, and then the mixture filtered. Hexane was added to the filtrate to precipitate an oily substance. The solvents were removed by decantation, and the obtained oily substance was dried in vacuum to obtain 1.71 g of the compound of this invention in the form of white hygroscopic crystals. The crystals were pulverized and thoroughly dried in vacuum. The melting point of the product was 77° to 79° C. (in a sealed tube).

Infrared Absorption Spectrum $\nu^{KBr}$, cm$^{-1}$: 3370, 1630, 1580, 1475, 1455, 1333, 1260, 1150, 950

Nuclear Magnetic Resonance Spectrum (D$_2$O) $\delta$: (Internal Standard: sodium 3-(trimethylsilyl)propanesulfonate) 3.19 (9H, s), 3.53 (2H, m), 4.05 (2H, m), 7.74 (4H, s)

Result of Elementary Analysis: C 49.3%, H 6.5%, N 9.6% Calcd. Value as $C_{12}H_{18}N_2O_4S \cdot 0.3H_2O$: C 49.4%, H 6.4%, N 9.6%

EXAMPLE 2

Synthesis of the Compound of this Invention 1.48 g (8.1 millimoles) of saccharin was added to 10 ml of water, and to the mixture added 2 g of an approximately 49% aqueous solution of choline hydroxide (containing 0.98 g (8.1 millimoles) of choline hydroxide) under agitation. After agitation at room temperature for about 20 minutes, all of the added saccharin was dissolved and the reaction was completed. The reaction mixture was concentrated under a reduced pressure, and the concentrated product was dissolved in 30 ml of acetone. Activated carbon was added to the solution, and then the mixture was filtered. Hexane was added slowly to the filtrate under agitation, and seed crystals were added when the solution became slightly cloudy, whereby crystals were separated. Additional hexane was added slowly to complete separation of crystals. The crystals were collected on a glass filter and rapidly dried in vacuum to obtain 1.07 g of white hygroscopic crystals. The crystals were dissolved again in acetone, and to the solution added hexane dropwisely under agitation to give crystals. They were collected and dried in vacuum to obtain the compound of this invention having a melting point of 78° to 79° C. (in a sealed tube).

Result of Ultimate Analysis: C 49.5%, H 6.6%, N 9.6% Calcd. Value as $C_{12}H_{18}N_2O_4S \cdot 0.3H_2O$: C 49.4%, H 6.4%, N 9.6%

EXAMPLE 3

Synthesis of the Compound of this Invention 2.05 g (10 millimoles) of sodium salt of saccharin was added to 10 ml of methanol, and to the solution added 1.40 g (10 millimoles) of choline chloride. After boiling for about one hour, the major portion of methanol was recovered under a reduced pressure. 15 ml of dichloromethane was added to the residue and the mixture agitated sufficiently. Undissolved sodium chloride was filtered off, and the filtrate was concentrated under a reduced pressure to remove the solvents, followed by drying in vacuum, to obtain the compound of this invention in the form of white hygroscopic crystals. Yield was 2.80 g.

The product was pulverized and dried thoroughly in vacuum. The product had a melting point of 76° to 78° C. (in a sealed tube).

EXAMPLE 4

Preparation of Wettable Powders 30 parts ("part" stands for "part by weight" throughout the following description) of the compound of this invention were mixed with 2 parts of white carbon and further mixed with 3 parts of sodium alkylethersulfonate and 2 parts of sodium alkylnaphthalenesulfonate acting as wetting agents. The mixture was further mixed with 63 parts of clay acting as a filler, and the admixture was mixed and then pulverized to prepare wettable powders.

EXAMPLE 5

Preparation of Granules 8 parts of the compound of this invention were mixed with 62 parts of clay and 26 parts of bentonite, and further mixed with 0.5 parts of alkylbenzenesulfonate and 3.5 parts of sodium ligninsulfonate, the latter-mentioned two compounds acting as disintegrators. To the mixture was added an appropriate amount of water, while mixing continuously, and then the obtained mixture granulated and dried, followed by sieving of grains to prepare granules.

EXAMPLE 6

Test for Appraisal of Effectiveness When Applied to Soil

Rice plants (Rice Plant Species: KOSHIHIKARI) were grown in synthetic resin pots each having a diameter of 6.5 cm until they were grown to the 3-leaf stage. One plot for each test included 4 pots in which 40 rice plants were grown. Onto the surface of the soil in each pot was applied 10 ml of a diluted formulation which was prepared by diluting wettable powders of Example 4 with water to a predetermined concentration. After the lapse of 14 days from the application of the chemicals, a suspension of rice blast fungus spores was sprayed uniformly to the rice plants for inoculation. After placing the pots in a humidified chamber maintained at 25° C. for one night, the pots were transferred to a room in which the environment was controlled artificially. After the lapse of 7 days from the inoculation of rice plant fungus spores, the number of lesions was counted and the preventive value was calculated from the following equation.

$$\text{Prevention Value (\%)} = \left[1 - \frac{\text{Average Number of Lesions Found in Treated Plot}}{\text{Average Number of Lesions Found in Untreated Plot}}\right] \times 100$$

The results are shown in Table 1.

TABLE 1

| Tested Chemicals | Amount of Effective Component Applied (g/10a) | Preventive Value (%) | Chemical Damage to Rice Plant |
| --- | --- | --- | --- |
| Compound of the Invention | 100 | 95 | None |
| Compound of the Invention | 60 | 88 | None |
| Compound of the Invention | 15 | 83 | None |
| ORYZEMATE | 100 | 78 | None |
| Sodium Salt of Saccharin | 100 | 84 | Somewhat Under- |

TABLE 1-continued

| Tested Chemicals | Amount of Effective Component Applied (g/10a) | Preventive Value (%) | Chemical Damage to Rice Plant |
|---|---|---|---|
| Untreated Plot | — | 0 | developed Growth |

EXAMPLE 7

Test for Appraisal of Effectiveness When Applied Under Water-Leaking Condition

Rice plants (Rice Plant Species: KOSHIHIKARI) of the 3-leaf stage transplanted to one pot of 100 cm² were subjected to test. One plot for each test included 5 pots in which 30 rice plants were grown. Each pot was filled with water so that the depth of water was about 3 cm, and a diluted formulation which was prepared by diluting wettable powders of Example 4 with water was placed on the surface of water so that the amount of chemical in the pot was adjusted to the value as shown in the following Table 2. The water in each pot was allowed to leak out to reduce the water depth by 1 cm per 1 day, and water was supplemented once a day throughout the test period. The rice plants were grown for 28 days, and then a suspension of rice blast fungus spores was sprayed at the 29th day so that the rice plants were inoculated with the spores. Immediately after the inoculation, the pots were transferred to a humidified chamber, and maintained therein for 24 hours. After the lapse of 24 hours, the pots were transferred to a greenhouse. At the day after 7 days from the inoculation of the spores, the number of lesions appearing on the leaves of the rice plants was counted. The preventive value was calculated similarly as in Example 6. Simultaneously, the number of tillers was checked, and the ratio of the number of tillers found in each treated plot applied with one of the chemicals to the number of tillers found in the untreated plot applied with no chemical was calculated.

The results of the test are shown in Table 2.

TABLE 2

| Tested Chemicals | Amount of Effective Component Applied (g/10a) | Preventive Value (%) | Ratio of Number of Tillers (vs. Untreated Plot) (%) |
|---|---|---|---|
| Compound of the Invention | 60 | 92 | 115 |
| Compound of the Invention | 15 | 76 | 103 |
| ORYZEMATE | 60 | 51 | 102 |
| ORYZEMATE | 15 | 48 | 98 |
| Sodium Salt of Saccharin | 60 | 27 | 76 |
| Sodium Salt of Saccharin | 15 | 10 | 89 |
| Untreated Plot | — | 0 | 100 |
| Untreated Plot | — | 0 | 100 |

EXAMPLE 8

Test for Appraisal of Effectiveness When Applied to Rice Plant Grown in Nursery Box Rice Plants (Rice Plant Species: KOSHIHIKARI) were grown in a thin nursery box of 20 cm × 30 cm until they were grown to the 3-leaf stage. The concentration of the chemical was adjusted to have a predetermined concentration, and the chemical was applied over the surface of the soil in a nursery box in which the rice plants were grown. After 8 days the rice plants were drawn out of the nursery box, the roots thereof were washed and then transplanted in a 100 cm² pot containing soil which had not been applied with any chemical. Each test plot included 4 pots in which 24 rice plants were grown. After the lapse of 17 days from the transplantation, a suspension of rice blast fungus spores was sprayed to the rice plants for inoculation. After being placed stationarily in a humidified chamber for 24 hours after the inoculation, the pots were transferred to a greenhouse. After the lapse of 7 days from the inoculation, the number of lesions appearing on the leaves was checked and the preventive value of each chemical was calculated similarly as in Example 6.

The results are shown in Table 3.

TABLE 3

| Tested Chemicals | Amount of Effective Component Applied (g/10a) | Preventive Value (%) | Chemical Damage to Rice Plant |
|---|---|---|---|
| Compound of the Invention | 1000 | 97 | None |
| Compound of the Invention | 100 | 94 | None |
| Compound of the Invention | 10 | 90 | None |
| Sodium Salt of Saccharin | 1000 | 97 | Poor Tillering |
| Sodium Salt of Saccharin | 100 | 86 | Somewhat Poor Tillering |
| Sodium Salt of Saccharin | 10 | 65 | Somewhat Poor Tillering |

EXAMPLE 9

Test for Appraisal of Effectiveness to Bacterial Leaf Blight of Rice Plants

Rice plants (Rice Plant Species: KINNANPU) were grown in a 1/5000 are pot for one and a half months, and a predetermined amount of a 8% granulated formulation as prepared in Example 5 was applied over the water surface of the pot. After the lapse of 5 days from the application, Xanthomonas oryzae was inoculated using a needle on leaves of rice plants. On the 21st day after the inoculation of Xanthomonas oryzae, the length of each lesions on the leaves of the rice plants was measured.

The results are shown in Table 4.

TABLE 4

| Tested Chemicals | Amount of Effective Component Applied (g/10a) | Average Length of the Lesions (cm) | Chemical Damage to Rice Plant |
|---|---|---|---|
| Compound of the Invention | 500 | 1.2 | None |
| Compound of the Invention | 240 | 2.4 | None |
| Untreated Plot | — | 10.1 | |

The compound of this invention is thus effective to prevent rice blast and bacterial leaf blight, both being serious problems in the growing of rice, for a long time without damaging rice plants. It exhibits marked effectiveness for the prevention of spread of such blights either by application to the soil of the paddy field (including application to the water surface) or by application to nursery pots or nursery beds. The compound of this invention has only slight toxicity to fishes, and therefore is of great practical utility.

We claim:
1. 1,2-benzoisothiazol-3(2H)-one 1,1-dioxide, ion(1-),2-hydroxy-N,N,N-trimethyl-ethanminium represented by the following formula (I):

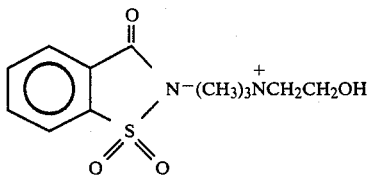 [I]

2. A plant protection composition for control of fungi and bacteria containing, as an effective component, 1,2-benzoisothiazol-3(2H)-one 1,1-dioxide, ion(1-), 2-hydroxy-N, N, N-trimethyl-ethanaminium represented by the following formula (I):

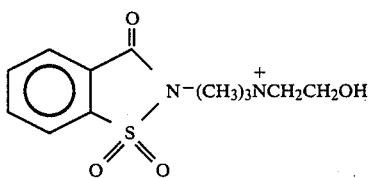 [I]

3. A method of protecting plants from blights, comprising an application of an effective amount of 1,2-benzoisothiazol-3(2H)-one 1,1-dioxide, ion(1-),2-hydroxy-N,N,N-trimethyl-ethanaminium represented by the following formula (I):

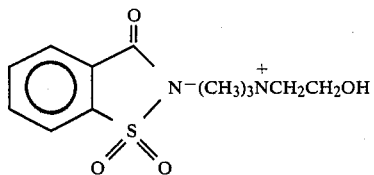 [I]

4. The method of protecting rice plants from rice blast according to claim 3, wherein 2 to 2000 g, per 10 ares, of 1,2-benzoisothiazol-3(2H)-one 1,1-dioxide, ion(1-),2-hydroxy-N,N,N-trimethyl-ethanaminum is applied to plowed soil or to water on the surface of the plowed soil.

5. The method of protecting rice plants from rice blast according to claim 3, wherein 2 to 2000 g, per 10 acres, of 1,2-benzoisothiazol-3(2H)-one 1,1-dioxide, ion(1-),2-hydroxy-N,N,N-trimethyl-ethanaminium is applied to the soil in the nursery pots or nursery bed before transplanting the rice plants to paddy field.

6. A method of protecting rice plants from bacterial leaf blight according to claim 3, wherein 2 to 2000 g, per 10 ares, of 1,2-benzoisothiazol-3(2H)-one 1,1-dioxide, ion(1-),2-hydroxy-N,N,N-trimethyl-ethanaminium is applied to the plowed soil or to water on the surface of the plowed soil.

* * * * *